United States Patent [19]

Lempert

[11] Patent Number: 5,139,022
[45] Date of Patent: Aug. 18, 1992

[54] METHOD AND APPARATUS FOR IMAGING AND ANALYSIS OF OCULAR TISSUE

[76] Inventor: Philip Lempert, 14 Cedar La., Ithaca, N.Y. 14850

[21] Appl. No.: 604,661

[22] Filed: Oct. 26, 1990

[51] Int. Cl.⁵ .................................................. A61B 3/10
[52] U.S. Cl. .................................. 128/633; 128/665; 351/206; 351/221
[58] Field of Search ................... 128/22, 23, 633, 665; 606/2, 6; 351/221, 205, 206, 246, 214, 207, 208

[56] References Cited

U.S. PATENT DOCUMENTS

| | | |
|---|---|---|
| 4,206,965 | 6/1980 | McGrew . |
| 4,213,678 | 7/1980 | Pomerantzeff et al. . |
| 4,541,856 | 9/1985 | Maillard et al. ......................... 65/29 |
| 4,573,778 | 3/1986 | Shapiro .............................. 351/219 |
| 4,702,576 | 10/1987 | Magnante . |
| 4,711,542 | 12/1987 | Ichihashi et al. . |
| 4,712,543 | 12/1987 | Baron .................................. 606/5 |
| 4,744,649 | 5/1988 | Niino et al. . |
| 4,863,261 | 9/1989 | Flammer ............................. 351/221 |
| 5,072,731 | 12/1991 | Taratuta et al. ....................... 128/633 |

OTHER PUBLICATIONS

"Device for Eliminating Corneal Light Reflections During Recording of Lateral Images with a Slip Lamp", by Bocca et al., published by Graefe's Archive for Clinical and Experimental Ophthalmology, 1986.
"Image-Pro: the Software Standard for Micro-Imaging", brochure by Media Cybernetics, Silver Springs, Md., 1990.
"The Objective Assessment of Cataract", by Brown et al., published by Eye, pp. 234-246, 1987.
"Evaluation of Photographic Method for Documentation of Lens Opacities", by Lee et al., published by Investigative Ophthalmology & Visual Science, vol. 31, No. 6, Jun. 1990.
"The Multi-Purpose Camera: A New Anterior Eye Segment Analysis System", by Sasaki et al., published by Ophthalmic Res, pp. 3-8, 1990.
Zoom Laser Diode Line Projector Systems (Model V-SCM-527/S7Z brochure, p. K-21, Newport Corporation, 1990.
Zoom Line Projector (Model V-SCM-OZ) brochure, p. K-22, Newport Corporation, 1990.
Straight-Line Generator Lens Laser Accessory, p. 104, Edmund Scientific Catalog, 1990.
"The Slit Lamp", pp. 324-326, in Clinical Visual Optics, by A. G. Bennet et al., published by Buttersworths, London, England, 1984.

*Primary Examiner*—William E. Kamm
*Assistant Examiner*—Kevin Pontius
*Attorney, Agent, or Firm*—Hopgood, Calimafde, Kalil, Blaustein & Judlowe

[57] ABSTRACT

A method and accompanying apparatus are provided for in vivo imaging of ocular tissue. In general, the method comprises providing a laser beam having an essentially planar configuration. The planar laser beam is directed through a cross-sectional portion of the ocular tissue, so as to illuminate the cross-sectional portion and cause the laser beam to be scattered by molecules in the ocular tissue. Then, at least a portion of the scattered laser light is detected so as to form a cross-sectional image of the ocular tissue. In general, the planar configured laser beam will have a slit-like cross-sectional dimension having essentially the same width dimension over the depth of field within which the largest depth dimension of the eye extends. These unique characteristics of the illumination beam permit the formation of clear, in-focus images detected at the image detection plane. The method and apparatus of the present invention can be used for objectively measuring the optical density of ocular tissue, as well as precisely measuring the physical dimension of ocular structures and their correct spatial relationships within the eye. In the case of the crystalline lens, the method and apparatus of the present invention can be utilized to produce in-focus cross-sectional images, from which the optical density of tissue comprising the lens can be precisely measured and thus the precise degree and location of cataract therewithin determined.

22 Claims, 8 Drawing Sheets

METHOD AND APPARATUS FOR IMAGING AND ANALYSIS OF OCULAR TISSUE

FIELD OF INVENTION

The present invention generally relates to a method and apparatus for objectively assessing in vivo the properties of ocular tissue, and more particularly to a method and apparatus for in vivo imaging and analysis of ocular tissue in an objective and quantitative manner for diagnostic and therapeutic purposes.

BACKGROUND OF INVENTION

In many diagnostic and therapeutic applications, there is great need to objectively quantify the optical density, shape and size of various ocular tissue, such as the crystalline lens and cornea. Regarding the crystalline lens, it is well known that the presence of a cataract at particular locations on the crystalline lens can effect the visual acuity and function of the eye. It is also known that the optical density of the cataract is related to the amount of light diffusion caused by increased size and coagulation of protein molecules in the crystalline lens, and that the more posterior the cataract the greater its affect on vision.

For years, prior art descriptions of cataracts have generally consisted of a morphologic statement, such as, nuclear, cortical, or posterior subcapsular. Such morphologic descriptions have been based primarily on the patient's potential visual acuity estimated using an acuity scope.

Prior art techniques in practice today are discussed in the paper "The Objective Assessment of Cataract," by Nicholas A. P. Brown. Among such prior art techniques is the use of a slit-lamp microscope for subjectively observing the visible features of the crystalline lens, which are recorded using the Oxford Clinical Cataract Classification and Grading System.

Recently, several different methods of photodocumentation and grading of lens opacities have been described for clinical and epidemiological use. For example, in the paper entitled "The Multi-Purpose Camera: A New Anterior Eye Segment Analysis System" published in Vol. 22 of Ophthalmic Research (1990), Saski et al. disclose a system for forming Scheimpflug slit images and retroillumination images of the lens using a Xenon flash lamp, a slit projection system and a CCD camera. In the paper entitled "Evaluation of Photographic Methods for Documentation of Lens Opacities," published in Investigative Ophthalmology and Visual Science, Vol. 31, No. 6, Jun. 1990, Lee et al. disclose a method of forming photographic slit and retroillumination images of the lens using the Oxford Cataract Camera from Halofax, of Hereford, England, and the Neitz Cataract Camera from Kowa Optical, of Torrance, Calif.

In general, while these prior art methods and systems can produce images of crystalline lens, both techniques and resulting images suffer from significant shortcomings and drawbacks.

In particular, with such prior art slit-lamp photo-imaging techniques, the depth of field and focus of these systems are severely limited and, therefore, permit focused illumination of only on the center of a lens nucleus while all other surrounding structure is illuminated with diverging unfocused light. Also, with prior art slit-lamp photo-imaging systems, neither the slit width or the luminance of the light beam can be maintained uniformly constant from image to image, or photo-examination session to photo-examination session. Consequently, comparative results cannot be made from one image to another to determine if the optical density of the lens is worsening in response to drug exposure, or disease process.

Furthermore, prior art slit-lamp photo-imaging techniques are incapable of providing accurate cross-sectional images of the eye which have correct spatial relationships between ocular structures. Also, such images are characterized by reflections occurring at optical interfaces within the eye which often distort important structural features.

Thus, there is great need for a method and apparatus that is capable of producing in vivo images of ocular tissue in a way which is free from the shortcomings and drawbacks accompanying the prior art.

Accordingly, it is primary object of the present invention to provide a method and apparatus for in vivo imaging and analysis of ocular tissue in an objective, quantitative manner.

It is a further object of the present invention to provide such a method and apparatus, from which cross-sectional images of ocular tissue can be formed over a high depth of field extending far beyond the thickness of the crystalline lens.

A further object of the present invention is to provide such a method and apparatus, from which accurate cross-sectional images of ocular tissue can be formed, with correct spatial relationships between ocular structures.

A further object of the present invention is to provide a method and apparatus for precisely measuring the physical dimensions of ocular structures and their correct spatial relationships within the eye.

An even further object of the present invention is to provide a method and apparatus for forming cross-sectional images of ocular tissue which enable precise localization of zones of increased optical density, such as cataract formation, in various locations of the crystalline lens.

Yet a further object of the present invention is to provide a laser-based ocular tissue analysis system in which cross-sectional digital images of the crystalline lens and surrounding ocular structures can be formed and from which the precise degree and location of optical density of the crystalline lens can be objectively determined using digital image analysis.

An even further object of the present invention is to provide such an ocular tissue analysis system in which the luminance and cross-sectional dimension of the laser illumination used to visualize the lens and form cross-sectional ocular images, can be maintained essentially uniformly constant from image to image, and photo-examination session to photo-examination session.

An even further object of the present invention is to provide such an ocular tissue analyzing system which includes a microscope and an image detector that uses laser illumination for visualizing and forming perfectly focused cross-sectional images entirely through the ocular tissue comprising the cornea and crystalline lens.

These and other objects of invention will become apparent hereinafter and in the claims.

SUMMARY OF INVENTION

According to one of broader aspects of the present invention, a method and accompanying apparatus are provided for in vivo imaging of ocular tissue. In general, the method comprises providing a laser beam having an essentially planer configuration. The planar laser beam is directed through a cross-sectional portion of the ocular tissue, so as to illuminate the cross-sectional portion and cause the laser beam to be scattered by molecules in the ocular tissue. Then, at least a portion of the scattered laser light is detected so as to form a cross-sectional image of the ocular tissue.

In general, the planar configured laser beam has a slit-like cross-sectional dimension having essentially the same width dimension over the depth of field within which the largest depth dimension of the eye extends. These unique characteristics of the illumination beam permit the formation of clear, in-focus images detected at the image detection plane.

The method and apparatus of the present invention can be used for objectively measuring the optical density of ocular tissue, as well as precisely measuring the physical dimension of ocular structures and their correct spatial relationships within the eye. In the case of the crystalline lens, the method and apparatus of the present invention can be utilized to produce in-focus cross-sectional images, from which the optical density of tissue comprising the lens can be precisely measured and thus the precise degree and location of cataract therewithin determined.

In the illustrated embodiment, the apparatus of the present invention is realized in the form of an optical tissue analysis system, which is capable of forming a plurality of cross-sectional images of the ocular tissue, with each image being specified at a different light scatter plane, defined within the ocular tissue. Preferably, the optical tissue analysis system comprises illumination beam directing means for directing the planar laser beam into the ocular tissue at a selected angle of incidence with respect to the ocular tissue, so that, for each selected angle of incidence, the laser light scatters principally in a different light scatter plane within the ocular tissue. The system also includes detecting means for detecting a portion of the scattered laser light from each different light scatter plane. On the basis of the plurality of acquired cross-sectional images, a three-dimensional image or model of the ocular tissue can be reconstructed and subsequently displayed along desired viewing directions.

BRIEF DESCRIPTION OF THE DRAWINGS

For a further understanding of the objects of the present invention, the detailed description of the illustrated embodiment is to be taken in connection with the following drawings, wherein.

DETAILED DESCRIPTION OF ILLUSTRATED EMBODIMENT

Figure 1A:
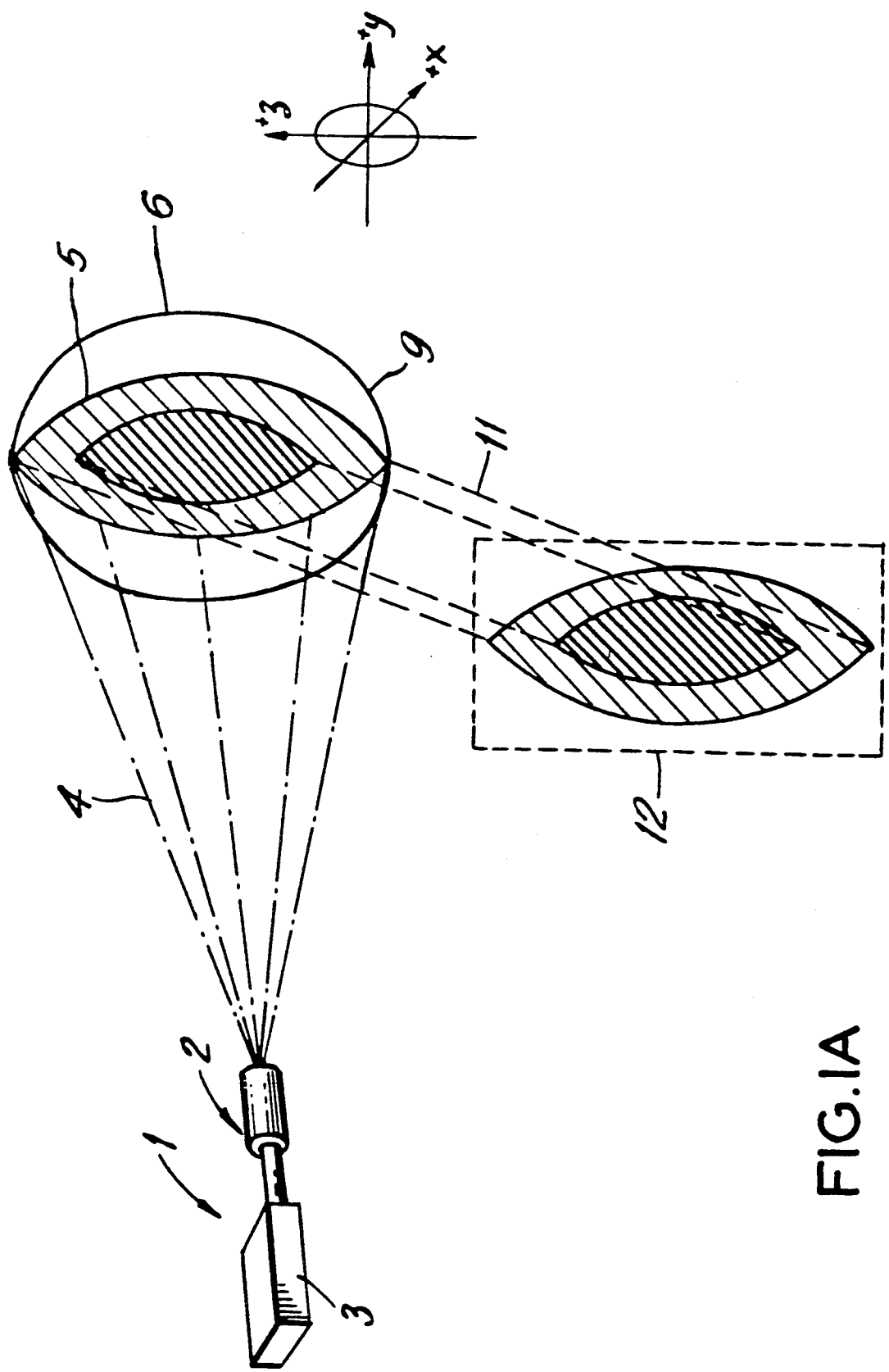
FIG. 1A is a schematic representation of the method of image formation according to the present invention, showing the illumination of a cross-sectional portion of a crystalline lens with an essentially planar laser beam of essentially uniform luminance and the detection of scattered laser light from the cross-sectional portion to form an image thereof at the image detection plane.
Figure 1B:
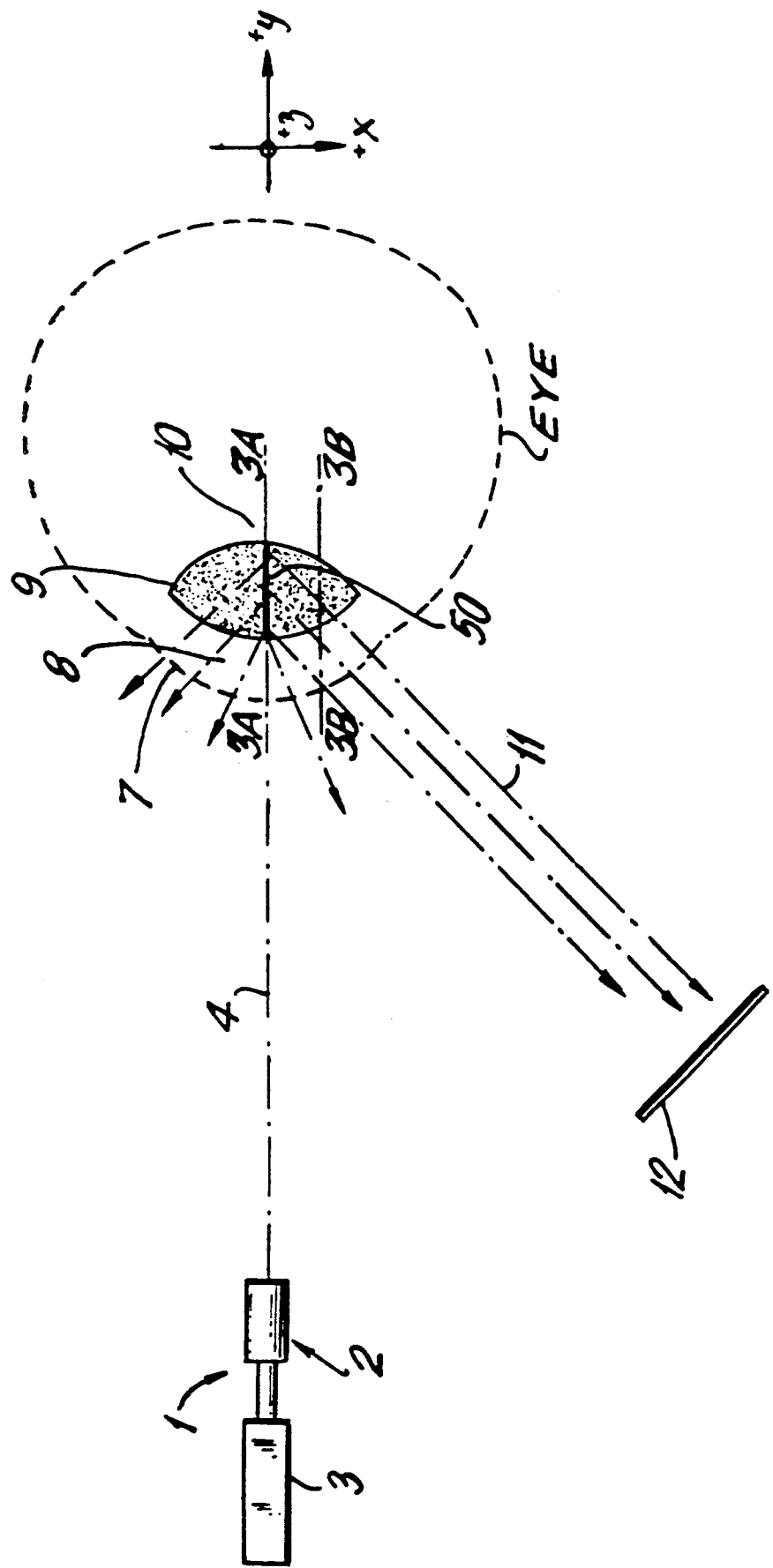
FIG. 1B is a schematic representation of the method of the present invention, illustrating the path of laser illumination and light scatter and detection, as viewed from along the Z-Y plane of the coordinate reference system of FIG. 1A.

Referring to FIGS. 1A and 1B in particular, the method of in vivo imaging ocular tissue according to the present invention, will first be described.

According to the present invention, a laser beam is used to illuminate ocular tissue so that laser light scattered by molecules comprising the tissue can be detected on an image detection plane positioned at some preselected scatter angle. An essential characteristic of the illumination laser beam of the present invention is that it has an essentially planar configuration and an essentially uniform luminance over each slit-like cross-section.

It has been discovered that by using an essentially planar laser beam having an essentially uniform luminance over each slit-like cross-section, wherein the width of each slit-like cross-section is essentially constant along the planar laser beam, it is possible to illuminate ocular tissue within the eye with a flux density which does not diverge along the depth of field, within which the largest depth dimension of the eye extends. Consequently, light scattered from ocular tissue anywhere along the propagation direction of the planar laser beam, will provide clear in-focus images detected at the image detection plane.

Generation of a planar laser beam in accordance with the principles of the present invention can be achieved using a commercially available zoom laser diode line projector system, such a Model V-SLM-S2Z from Newport Corporation of Mountain Valley, Calif. In general, the zoom laser-diode line projector system 1 comprises a line projector head 2 and a power supply 3. The line projector head 2 includes a 1.5 milliwatt laser, and electronic circuitry for regulation of optical power output and protection of the laser diode against line transients and electromagnetic noise. In addition to having an input for modulation of the laser output, line projector head 2 also includes beam shaping optics for structuring the optical distribution into a planar configuration. Mechanical movements are also provided for easy adjustment of the lens for planar beam geometry. Focus adjustment is also provided to allow the user to control the line width at any desired standoff. Line widths as narrow as 0.004 inch are achievable by adjustment of focus control, whereas line length is adjustable by controlling beam divergence.

As illustrated in FIGS. 1A and 1B, in vivo imaging is achieved by directing at a preselected angle of incidence the essentially planar laser beam 4 through a cross-sectional portion of ocular tissue 6. In the example shown FIG. 1A, the ocular tissue comprises the crystalline lens, whereas in FIG. 1B the ocular tissue comprises cornea 7, anterior cortex 8, crystalline lens 9 and posterior cortex 10. As illustrated, incident planar laser beam 4 is directed along a line of incidence 50 to illuminate a cross-sectional portion (i.e., light scatter plane) 5 of the ocular tissue, thereby causing planar laser beam 4 to be scattered by molecules in that light scatter plane. Then, at some preselected angle of scatter, at least a portion of scattered laser light 11 is detected at an image detection plane 12 so as to form a cross-sectional image of the illuminated ocular tissue. As will be described in greater detail hereinafter, detection of the cross-sectional scatter image at image detection plane 12 can be achieved using one of a number of image detection techniques.

In order to maintain the eye relatively stationary with respect to planar illumination beam 4 and image detection plane 12, the patient's head should be steadied by a conventional chin and forehead rest (not shown). In the steadied position, the patient faces the planar laser beam, which is oriented at about 45 degrees to the image detection axis, extending perpendicular from the image detection plane.

Figure 2:
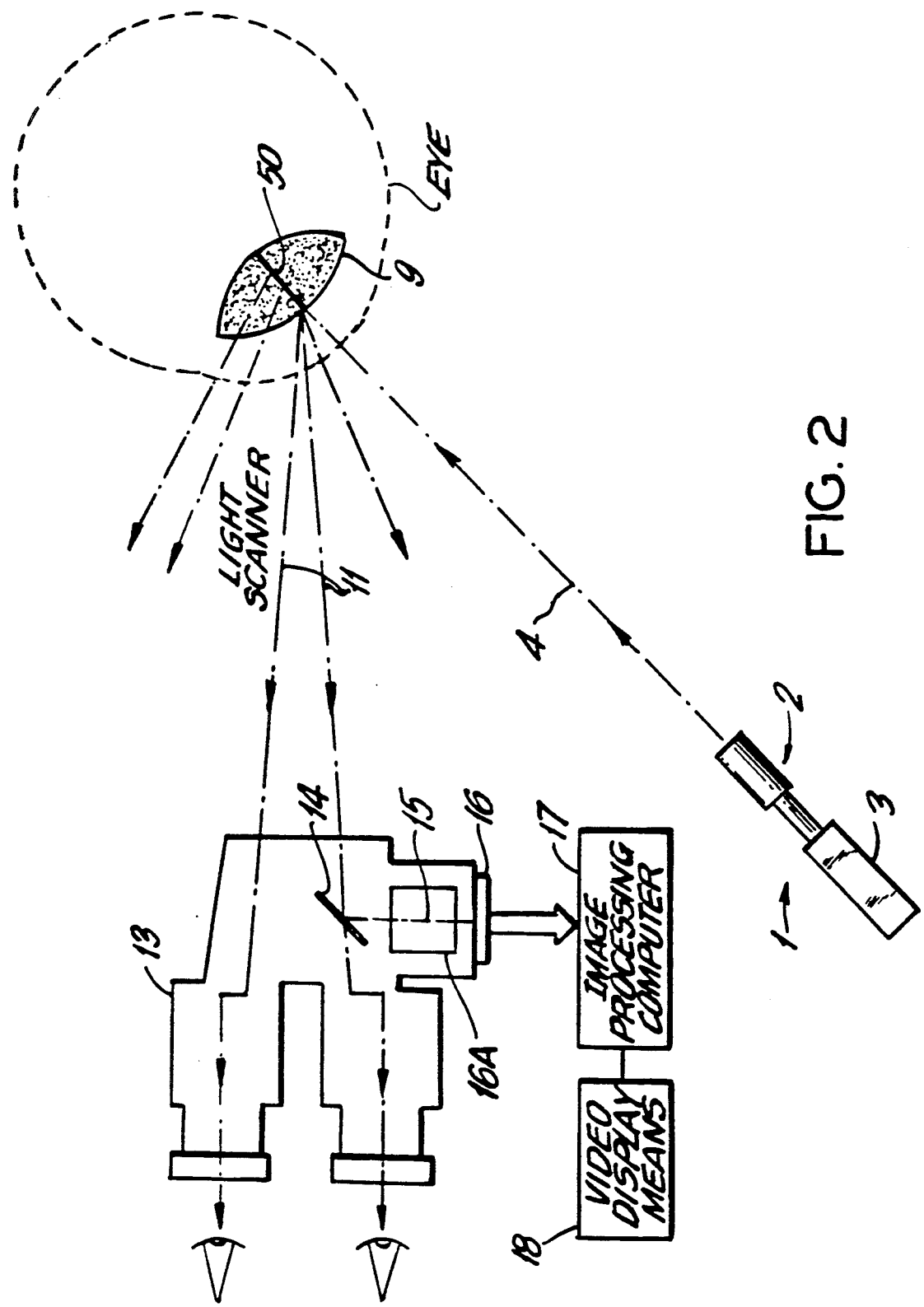
FIG. 2 is a schematic representation of the first embodiment of the present invention realized as a binocular microscopic and scatter image detection and analysis system.
Figure 3A:
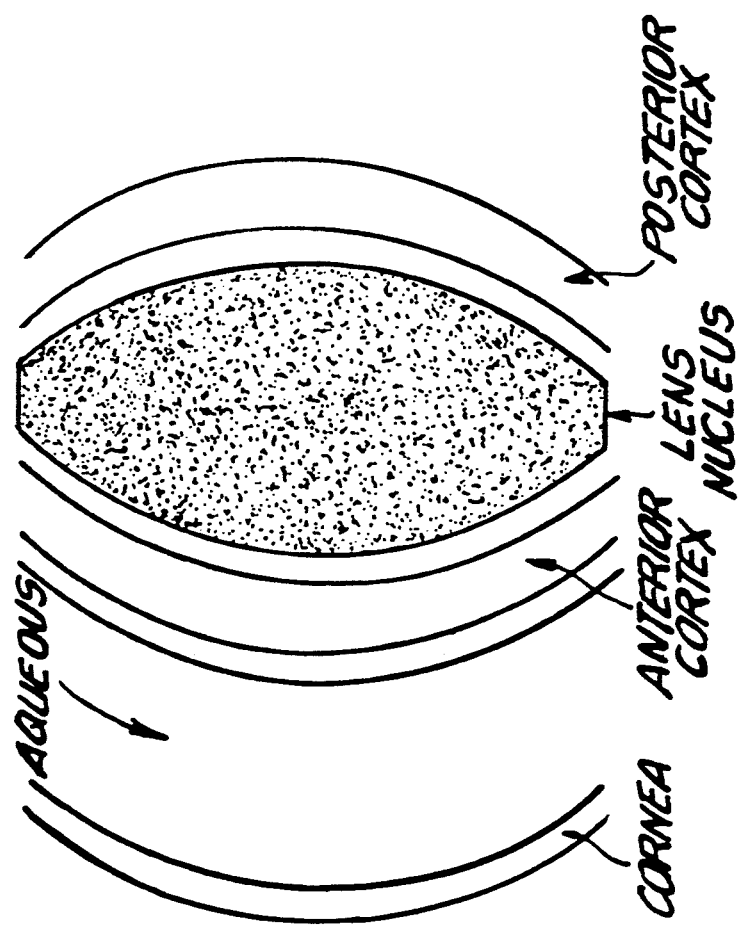
FIG. 3A is a schematic representation of a detailed scatter image of a cross-sectional portion of the eye shown in FIG. 1B, taken along line 2A—2A, representative of the central portion of the crystalline lens.
Figure 3B:
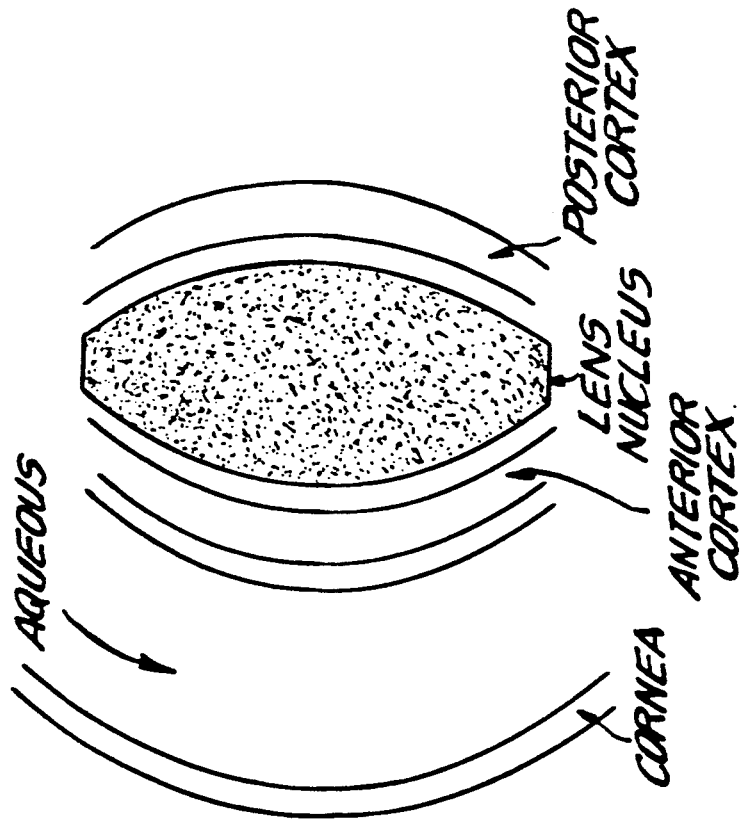
FIG. 3B is a schematic representation of a detected scatter image of a cross-sectional portion of the eye shown in FIG. 1B, taken along line 2B—2B, representative of an edge portion of the crystalline lens.

As shown in FIG. 2, the scattered light is preferably focused through the optics of a binocular microscope system 13, so that the user can visualize the cross-sectional image formed under the illumination of planar laser beam 4. Also, as illustrated, a beam splitter 14 is provided along an optical path in binocular microscope system 13. The function of beam splitter 14 is to split the beam of scattered light 11 from the cross-sectional portion of the crystalline lens, and direct the produced light beam 15 onto photo-electronic image detector 16 to form a digitized cross-sectional image. Notably, scatter light beam 15 is focused by optics 16A to form the cross-sectional image on the image detection plane of image detector 16.

Preferably, image detector 16 is a charged coupled device (CCD) video camera comprising an array of photoresponsive units, and is used in conjunction with a laser 2 producing a planar laser beam output having a wavelength preferably in the range of 600 to 650 nanometers. With this arrangement, a digitized cross-sectional image of the ocular tissue can be produced, while taking advantage of the CCD camera's sensitivity over this range of wavelengths. Also at the recommended power level of, for example, 1.5 milliwatts, the retina can be continuously exposed to the planar laser beam without risk of thermal injury. In such an embodiment, the digitized cross-sectional image consists of a plurality of pixels, each pixel having an intensity value. In a conventional manner, using a grey-scale of 0–255, the intensity of each pixel can be quantized with great precision, and so too the optical density of the ocular tissue represented by the pixel values comprising the image.

In order to measure the optical density of ocular tissue, such as the crystalline lens, over particular zones of interest, the video output of CCD image detector 16 is provided to a conventional image processing computer 17 programmed with comprehensive image processing software that is capable of performing a variety of functions, including, for example, image analysis, image measurement and image processing. Such software is commercially available from Media Cybernetics, of Silver Springs, Md., under the trade name Image-Pro ™. Image processing computer 17 also includes a video display device 18 for visually displaying the images acquired at the image detection plane of CCD camera 16.

Figure 4:
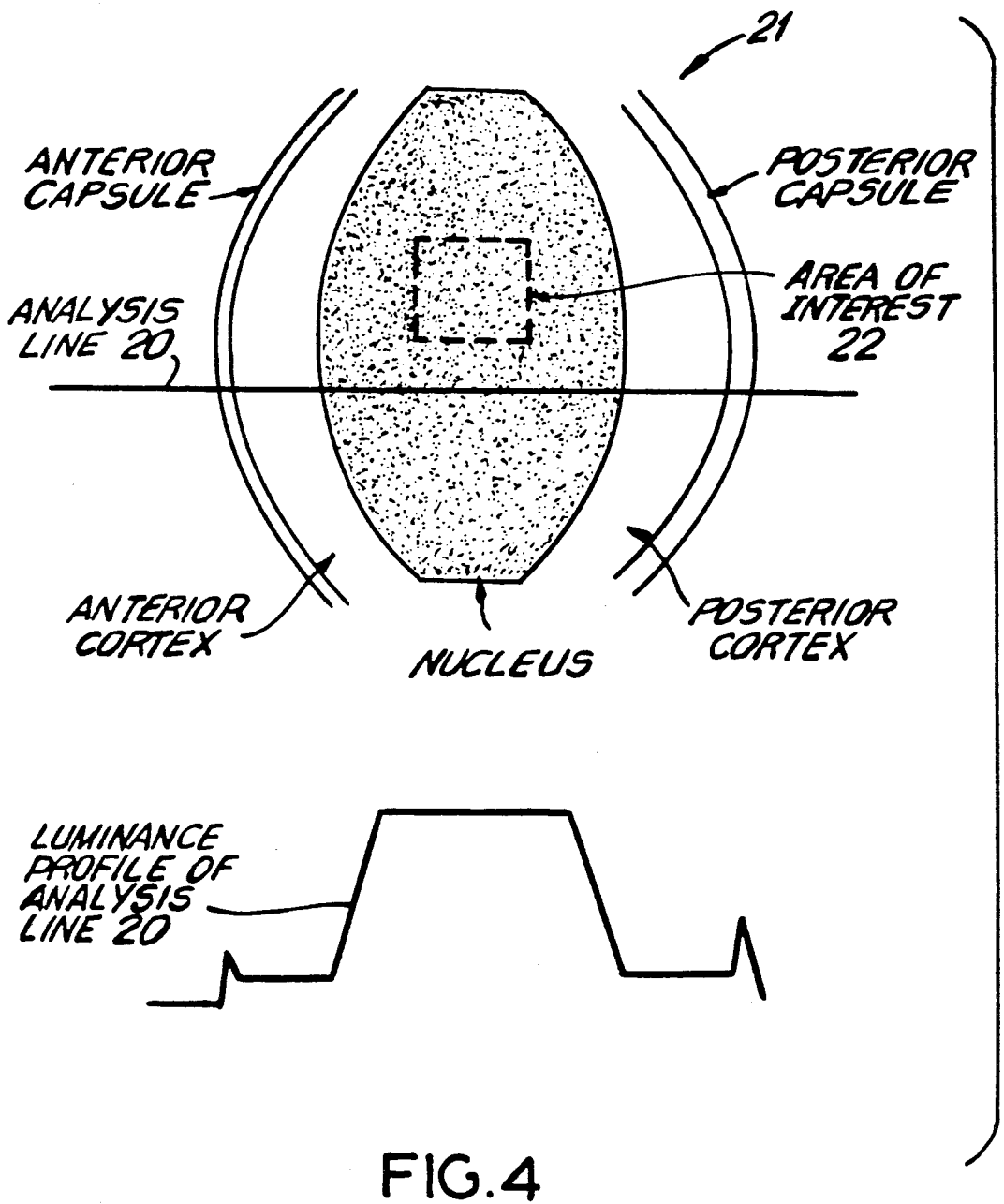
FIG. 4 is a schematic representation of a detected scatter image formed in accordance with the method of the present invention, illustrating the various ocular structures within the image and the use of digital image processing to provide the luminance (i.e., optical density) profile along a selected line of analysis.

An example of several types of image analysis that would typically be performed upon the cross-sectional images, is illustrated in FIG. 4.

As shown, in FIG. 4, digitized image 21 is displayed on video display device 18. A line of analysis 20 is selected, in this particular example, extending through the entire cross-sectional image 21 of the anterior cortex, the nucleus and the posterior cortex of the crystalline lens. Then using the image analysis function of Image-Pro ™ software, the luminance profile along the selected analysis line, can be determined and displayed. From the luminance profile, structural transitions and relative optical density in the ocular tissue can be readily discerned.

By performing histographic analysis within selected areas of interest 22 in digitized cross-sectional image 21, it is possible to determine the optical density of certain portions of the patient's crystalline lens and thus the precise degree and location of cataract. Notably, with a pixel grey scale of 0–255, optical density within ocular tissue can be quantified with the same degree of precision. Together with the constant luminance over each slit-like cross-section of the planar laser illumination beam 4 and the constant sensitivity of photoelectronic image detector 16, consistent cross-sectional images of ocular tissue can be produced and stored in a repeated manner without variation in the measurement of optical density. In this way, cross-sectional images of a patient's crystalline lens, for example, can be produced, appropriately indexed as to location in the eye, and thereafter stored. At a subsequent date after, for example, exposure to cataractogenic factors or suitable drug therapy for cataract, additional cross-sectional images can be produced at the same location within the crystalline lens. Since the image formation conditions of the present invention can be maintained essentially constant during different image formation sessions, meaningful comparisons among these images can be made to determine the progress of the cataract. Also, owing to the constancy of the image formation conditions and the essentially non-diverging flux density along the width dimension of the planar illumination beam, images of the crystalline lens along a number of parallel cross-sections can be formed, stored and compared to determine the location and degree of cataract in the crystalline lens.

By performing image measurement functions of Image-Pro ™ software upon the detected cross-sectional image, the distances between and the areas and perimeters of various ocular structures can be precisely computed in a conventional manner using geometrical techniques. For a discussion on such measurements please see Systems of Ophthalmology, Vol. 5, Ophthalmic Optics and Refraction, p. 109, by Duke Elder, published by CV Mosby, St. Louis, 1970; and Clinical Visual Optics, p. 331, by Bennett and Rubbett, published by Buttersworth, London, 1984. Such measurements can be most useful in properly fitting a patient with an intracapsular intraocular lens that fits snugly into the capsular bag without the necessity of elastic haptics. With the method of the present invention, it is thus possible to precisely determine a patient's Crystalline lens specifications, i.e., exterior and posterior curvature and diameter, thereby allowing the use of a new class of hapticless intraocular lenses.

Figure 5:
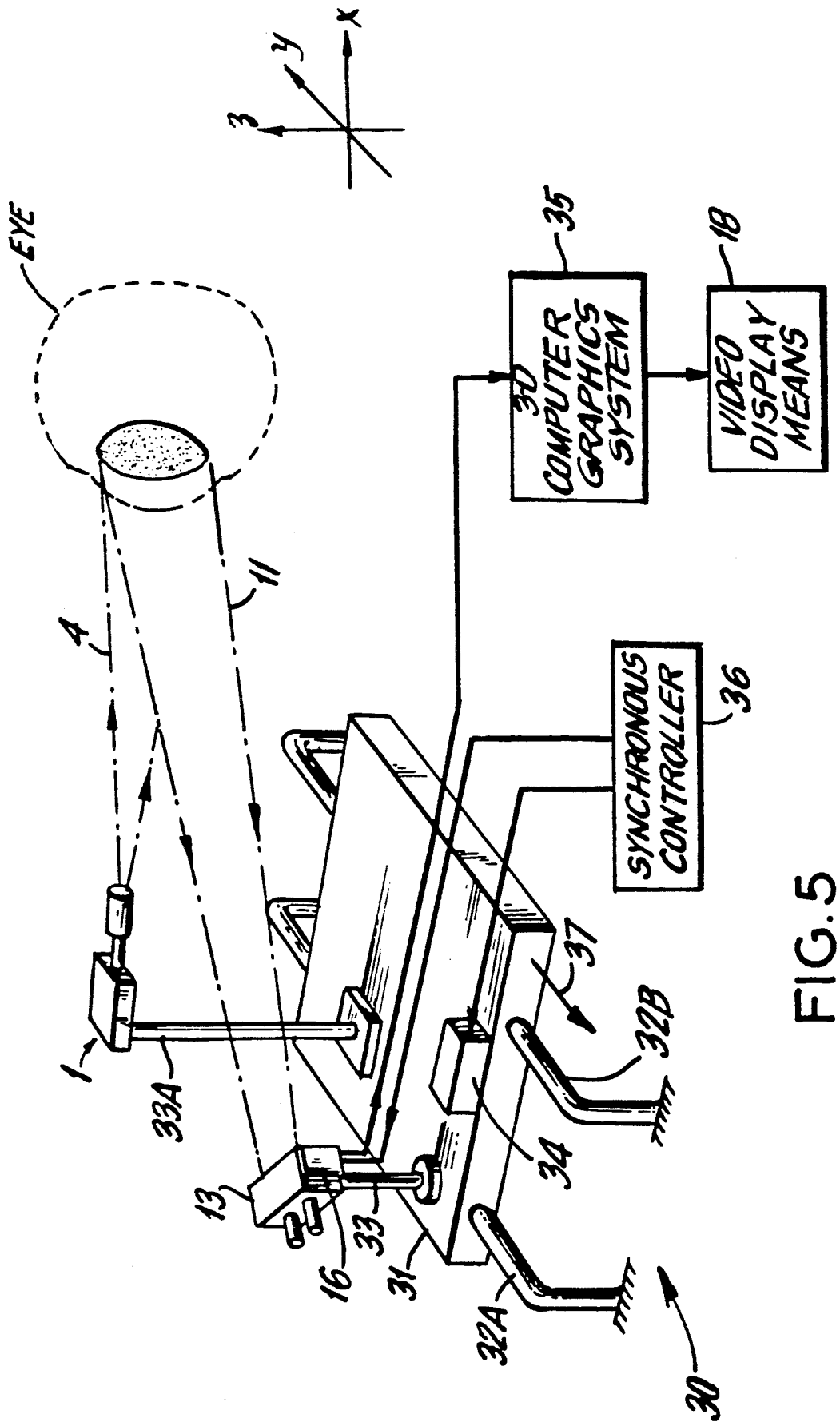
FIG. 5 is a schematic representation of the second embodiment of the apparatus of the present invention, realized as an ocular tissue analyzing system including a binocular microscope and scatter image detection and analyzing subsystem capable of forming a plurality of cross-sectional images of ocular tissue taken at different angles of illumination incidence, and reconstructing these cross-sectional images to form a three-dimensional image of the ocular tissue.
Figure 6:
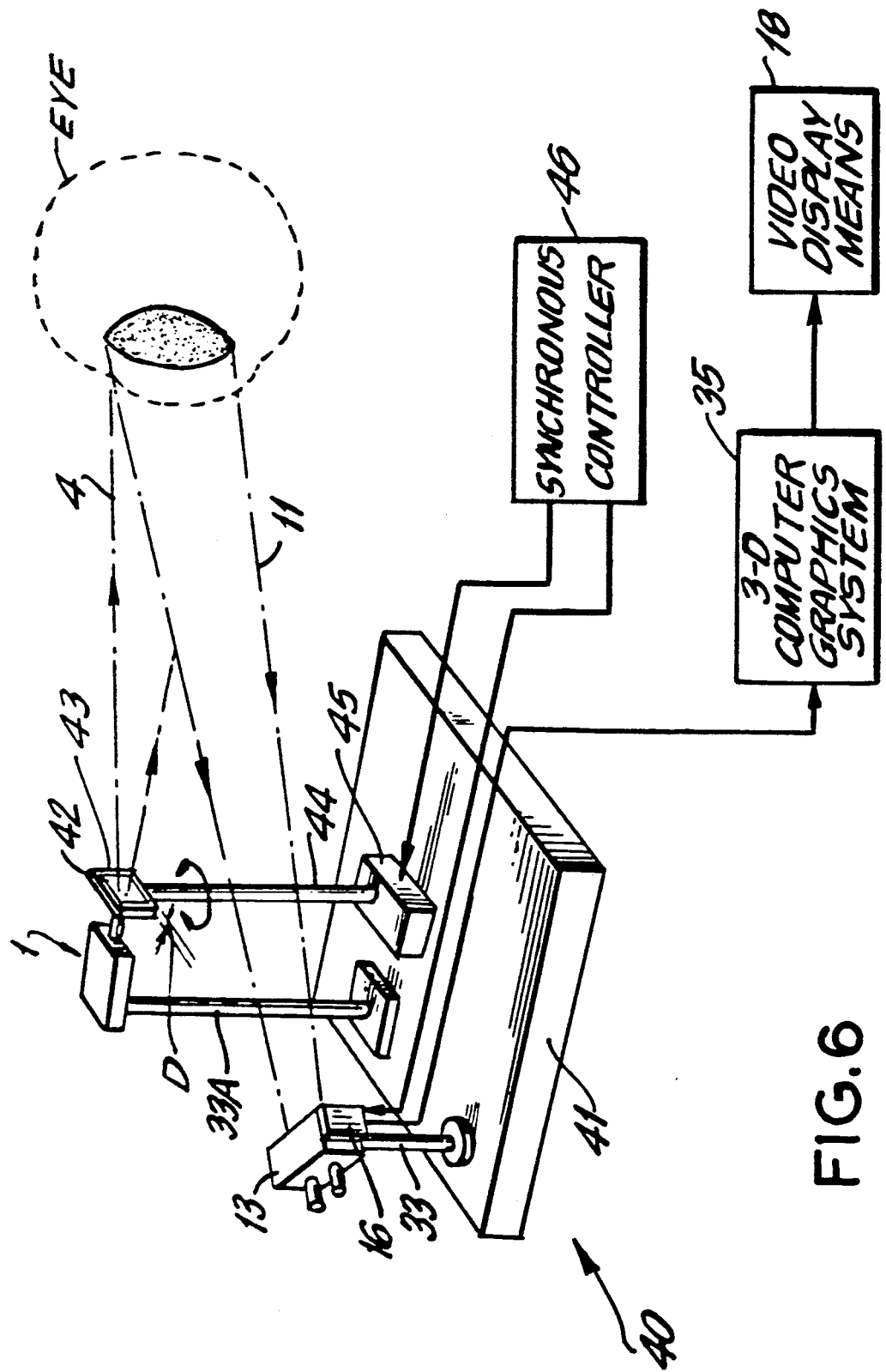
FIG. 6 is schematic representation of the third embodiment of the apparatus of the present invention, realized as an ocular tissue analyzing system including a binocular microscope and scatter image detection and analyzing subsystem capable of forming a plurality of cross-sectional images of ocular tissue taken at different angles of illumination incidence, and reconstructing these cross-sectional images to form a three-dimensional image of the ocular tissue.

In order to produce a three-dimensional visual model of ocular tissue such as the crystalline lens, either of the ocular tissue analyzing systems shown in FIGS. 5 and 6 can be used. In general, each system produces planar laser beam 4 for the purpose of illuminating, in a sequential manner, a plurality of parallel cross-sections of ocular tissue. As in the previously described embodiment, light scatter 11 from each cross-section is sequentially detected at the image detector plane, whereupon the detected image is stored or otherwise recorded. Thereafter, the plurality of cross-sectional images are reconstructed in a conventional computer graphics system having three-dimensional modeling capabilities. Two-dimensional views of the reconstructed model can then be examined along desired viewing directions provided by the computer graphics system.

In FIG. 5, ocular tissue analyzing system 30 comprises a platform 31, which is adapted to move along a pair of spaced-apart rails 32A and 32B, which are fixed relative to a stationary base portion (not shown). Preferably, the base portion will be of a height sufficient to permit the user to view the eye through binocular microscope system 13 mounted above platform 31 by way of a first support stand 33. A stepper motor and an appropriate gearing mechanism 34 is provided for effectuating sequential movement of platform 31 relative to rails 32A and 32B and stationary base portion. As illustrated in FIG. 5, planar laser beam source 1 and binocular microscope system 13 of FIG. 2 are fixedly mounted to platform 31 by way of first and second support stands 33 and 34, respectively. Preferably, these support stands are adjustable so that the optical axes of laser beam source 1 and microscope system 13 can be adjusted to lie within substantially the same optical planes. Also, in this embodiment each selected line of incidence of the planar illumination beam and the scatter angle of the image detection plane are fixed at an angle of about 45 degrees.

Figure 5A:
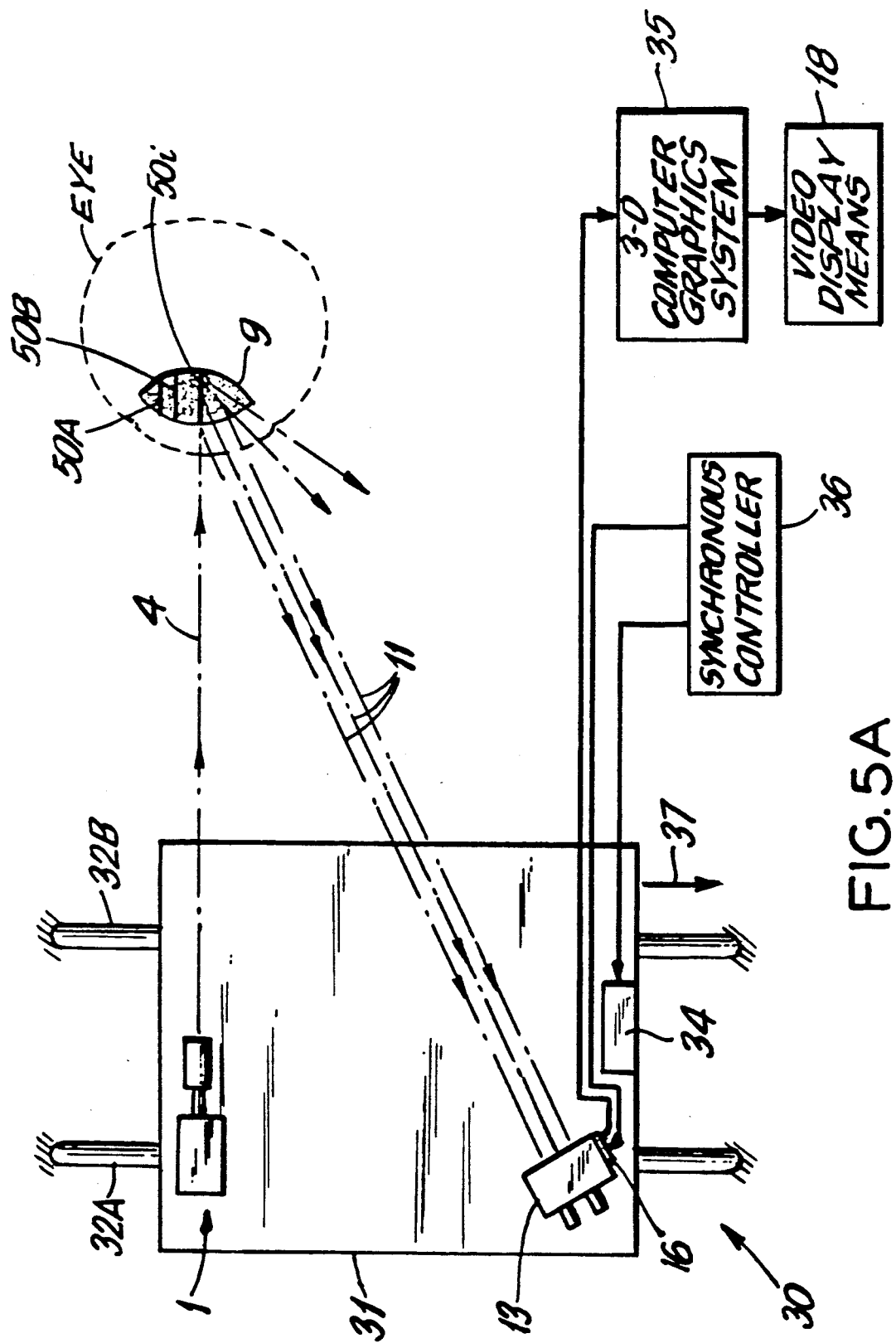
FIG. 5A is a schematic representation of the second embodiment of the apparatus of the present invention, as view from along X-Z plane of the coordinate reference system of FIG. 5.

As in FIG. 2, microscope system 13 of FIGS. 5A and 5B also includes a beam splitter 14 for forming a light scatter beam which is directed onto photoelectronics image detector 16. As illustrated in FIGS. 5A and 5B, the output of image detector 16 is provided to conventional 3-D computer graphics system 35, which includes video monitor 18, as described hereinabove. A sequential controller 36 is also provided for synchronously controlling the movements of platform 31 with respect to stationary base, as well as for transferring detected images from image detector 16 to 3-D computer graphics system 35.

At the beginning of an image acquisition process, platform 31 is positioned so that illumination beam 4 passes through a line of incidence 50A, co-planar with an end most portion of crystalline lens 9. During the first image acquisition cycle, planar laser beam 4 from source 1 is directed into the ocular tissue along line of incidence 50A which is substantially parallel to the optical axis of the eye. Along this line of incidence, planar laser beam 4 illuminates molecules lying along a light scatter plane co-planar with the planar laser beam and scatters the laser light. While under the control of synchronous controller 36, image detector 16 detects a portion of the scattered laser light which is focused through the optics of image detector 16 to form the scatter image. The scatter image is detected by image detector 16 which is positioned at a scatter angle which is fixed with respect to the selected line of incidence, along which planar laser beam 4 propagates. The detected scatter image is then transferred to 3-D computer graphics system 35 for storage. Synchronous controller 36 then moves platform 31 a very small lateral increment with respect to the eye, in the direction of the reference arrow 37. This lateral displacement permits planar laser beam 4 to be once again directed into the ocular tissue, but this time along a line of incidence 50B and within a light scatter plane which is offset, yet parallel to the previous line of incidence 50A and corresponding light scatter plane. The detected cross-section image along line of incidence 50B is then transferred from image detector 19 to 3-D computer graphics system 35 for storage.

The above-described process of incrementally moving platform 31 to sequentially offset the line of incidence from the previous line of incidence and to synchronously acquire, transfer and store the detected image, is repeated a number of times under the control of synchronous controller 36 until a sufficient number of parallel cross-sectional images have been acquired. Thereafter, these images are used to compute one or more reconstructed three-dimensional image of the ocular structure under examination. Such 3-D image reconstructions can be produced using conventional programming techniques, then stored in memory of computer graphics system 35, and subsequently displayed along desired or selected viewing directions.

The operation of ocular tissue analysis system 40 is similar in many respects to system 3 illustrated in FIGS. 5 and 5A. For example, laser source 1 and microscope system 13 are fixedly mounted onto a platform 41 in a manner described above in connection with the second embodiment. There are several differences, however. Platform 41 is stationary with respect to the eye of the patient. Also, to laterally displace planar laser beam 4 with respect to the patient's eye, a glass plate 42 of a predetermined thickness D is mounted to a support frame 43. In turn, support frame 43 is supported by a post 44 which is rotatable with respect to platform 41 by a stepper motor 45 operated under the control of a synchronous controller 46. As stepper motor 45 is driven by synchronous controller 46, glass plate 42 is rotated a preselected amount, thereby effectuating desired incremental lateral displacement of the planar laser beam along a selected line of incidence, preferably parallel with the optical axis of the eye under examination.

At the beginning of the image acquisition process, refractive plate 42 is preferably substantially perpendicular with planar illumination beam 4. During the first image acquisition cycle, the refractive plate 42 remains in its original or initial position, and the end most cross-section of ocular tissue is illuminated and the scatter image detected by image detector 16. After synchronously transferring the first detected image to the 3-D computer graphics system 35 under control of synchronous controller 46, refractive plate 42 is rotated by a small angular increment to displace slightly the line of incidence of planar illumination beam 4 away from the previously selected line of incidence. A cross-section of ocular tissue parallel to its first cross-section (i.e., light scatter plane) is thusly illuminated and the scattered light is detected by image detector 16, whereupon this second cross-sectional image is transferred to 3-D computer graphics system 35 for storage. The above image acquisition cycle is repeated a number of times under the control of synchronous controller 46 until a sufficient number of images are acquired for 3-D image reconstruction, as discussed above.

In the illustrated embodiments, photoelectronic image detecting apparatus and digital image processing techniques are utilized in carrying out the present invention. However, photographic image recording techniques and optical density measurement techniques for photographic images can also be to carry out the present invention with expectedly good results.

While the particular embodiments shown and described above have proven to be useful in many applications in the ophthalmic art, further modifications of the present invention herein disclosed will occur to persons skilled in the art to which the present invention pertains, and all such modifications are deemed to be within the scope and spirit of the present invention defined by the appended claims.

What is claimed is:

1. A method for in vivo imaging of ocular tissue, comprising the steps:
   (a) providing a laser beam having an essentially planar configuration;
   (b) directing said laser beam through a cross-sectional portion of said ocular tissue, so as to illuminate said cross-sectional portion and cause said laser beam to be scattered by molecules in said ocular tissue; thereby forming scattered laser light and
   (c) detecting at least a portion of said scattered laser light so as to form a cross-sectional image of said ocular tissue.

2. A method of claim 1, wherein step (a) comprises providing a laser beam having an essentially planar configuration and a slit-like cross-sectional dimension of an essentially uniform luminance.

3. The method of claim 1, which further comprises
   (d) analyzing said detected cross-sectional image of said ocular tissue, and determining optical properties of said cross-sectional portion of ocular tissue.

4. The method of claim 1, wherein step (c) comprises forming a digitized cross-sectional image of said ocular tissue, said digitized cross-sectional image consisting of a plurality of pixels, each said pixel having an intensity value.

5. The method of claim 4, wherein step (d) comprises analyzing at least a region of said digitized cross-sectional image by processing the intensity values of the pixels representing said region.

6. The method of claim 4, wherein said digitized cross-sectional image is formed by focusing said portion of scattered light onto an image detecting array of photo responsive elements.

7. The method of claim 6, wherein step (a) comprises generating from a laser, said laser beam having a wavelength in the range of about 600 to about 650 nanometers, and step (c) comprises detecting said cross-sectional image on said image detecting array comprising a plurality of operationally associated charge coupled devices.

8. The method of claim 7, wherein step (a) comprises producing a laser beam from a lasing device and guiding said laser beam through a telescoping optical system to produce said essentially planar laser beam.

9. The method of claim 1, wherein step (b) comprises directing said laser beam through a cross-sectional portion of the crystalline lens in a human eye, so as to illuminate said cross-sectional portion and cause said planar laser beam to be scattered by molecules in said crystalline lens, and wherein step (c) comprises detecting at least a portion of said scattered laser light so as to form a cross-sectional image of said crystalline lens.

10. The method of claim 1 which further comprises forming a plurality of cross-sectional images of said ocular tissue, each said cross-sectional image being specified at a different light scatter plane defined within said ocular tissue.

11. The method of claim 10, which further comprises forming a three-dimensional image of said ocular tissue on the basis of said plurality of said cross-sectional images.

12. The method of claim 11, wherein each said cross-sectional image is formed by
   directing said laser beam into said ocular tissue, at a selected line of incidence with respect to said ocular tissue so that, for each said selected line of incidence, said laser light scatters principally in a single light scatter plane within said ocular tissue, and
   detecting a portion of said scattered laser light from said single light scatter plane, at a fixed angle of scatter with respect to said selected line of incidence.

13. The method of claim 11, wherein each said cross-sectional image is formed by
   directing said laser beam into said ocular tissue at selected line of incidence with respect to said ocular tissue so that, for each said selected line of incidence, said laser light scatters principally in a different light scatter plane within said ocular tissue, and
   detecting a portion of scattered laser light from each said different light scatter plane, at a scatter angle which is fixed with respect to said selected line of incidence, wherein each said line of incidence is selected by repositioning together means used for directing said laser beam and for detecting said scattered laser light.

14. Apparatus for in vivo imaging of ocular tissue, comprising:
   laser beam provision means for providing a planar laser beam having an essentially planar configuration;
   laser beam directing means for directing said laser beam through a cross-sectional portion of said ocular tissue, and for causing said laser beam to be scattered by molecules in said ocular tissue; thereby forming scattered laser light and image detection means for detecting at least a portion of said scattered laser light so as to form a cross-sectional image of said ocular tissue.

15. The apparatus of claim 14, which further comprises
analyzer means for analyzing said detected cross-sectional image of said ocular tissue, and determining optical properties of said ocular tissue, at said cross-section portion.

16. The apparatus of claim 15, wherein said image detection means comprises an image detecting array capable of forming a digitized cross-sectional image of said ocular tissue, said digitized cross-sectional image consisting of a plurality of pixels, each said pixel having an intensity value.

17. The apparatus of claim 16, wherein said analyzer means is capable of analyzing at least a region of digitized cross-sectional image by processing the intensity values of the pixels representing said region.

18. The apparatus of claim 14, wherein said laser beam provision means comprises a laser and a optical system, said laser producing a laser beam which is focused by said optical system to produce said essentially planar laser beam.

19. The apparatus of claim 14, which further comprises means for forming a plurality of cross-sectional images of said ocular tissue, each said cross-sectional image being specified at a different light scatter plane defined within said ocular tissue.

20. The apparatus of claim 19, which further comprises three dimensional image forming means for forming a three-dimensional image of said ocular tissue on the basis of said plurality of said cross-sectional image.

21. The apparatus of claim 19, wherein said three dimensional image forming means comprises
directing means for directing said laser beam into said ocular tissue, at a selected line of incidence with respect to said ocular tissue, so that, for each said selected line of incidence, said laser light scatters principally in a different light scatter plane within said ocular tissue, and
detecting means for detecting a portion of said scattered laser light from said different light scatter plane, at a fixed angle of scatter with respect to said selected line of incidence.

22. The apparatus of claim 19, wherein said three-dimensional image forming means comprises
directing means for directing said laser beam into said ocular tissue at a selected line of incidence with respect to said ocular tissue so that, for each said selected line of incidence, said laser light scatter principally in a different light scatter plane within said ocular tissue,
detecting means for detecting a portion of scattered laser light from each said different light scatter plane, at a scatter angle which is fixed with respect to said selected line of incidence, and
positioning means for positioning together said directing means and said detecting means so that each said line of incidence can be selected while maintaining said scatter angle fixed with respect to said selected line of incidence.

* * * * *